US012746092B2

(12) United States Patent
Sodha et al.

(10) Patent No.: US 12,746,092 B2
(45) Date of Patent: Sep. 29, 2026

(54) HYDROGEL-BASED ULTRASONOGRAPHY PROBE STABILIZER

(71) Applicant: Rhode Island Hospital, Providence, RI (US)

(72) Inventors: Neel R. Sodha, Providence, RI (US); Preston Nicely, Providence, RI (US); Allison Navarrete-Welton, Providence, RI (US); Reetam Ganguli, San Jose, CA (US); Amy Oh, Providence, RI (US)

(73) Assignee: Rhode Island Hospital, Providence, RI (US)

( * ) Notice: Subject to any disclaimer, the term of this patent is extended or adjusted under 35 U.S.C. 154(b) by 362 days.

(21) Appl. No.: 18/494,667

(22) Filed: Oct. 25, 2023

(65) Prior Publication Data

US 2024/0130827 A1 Apr. 25, 2024
US 2024/0225777 A9 Jul. 11, 2024

Related U.S. Application Data

(60) Provisional application No. 63/380,916, filed on Oct. 25, 2022.

(51) Int. Cl.
*A61B 90/00* (2016.01)

(52) U.S. Cl.
CPC ........ *A61B 90/37* (2016.02); *A61B 2090/378* (2016.02)

(58) Field of Classification Search
CPC .......................... A61B 2090/378; A61B 90/37
See application file for complete search history.

(56) References Cited

U.S. PATENT DOCUMENTS

| | | | | |
|---|---|---|---|---|
| 5,505,205 | A | 4/1996 | Solomon et al. | |
| 6,126,607 | A | 10/2000 | Whitmore et al. | |
| 7,931,596 | B2 | 4/2011 | Rachlin et al. | |
| 2005/0203410 | A1* | 9/2005 | Jenkins | A61B 8/4488 600/459 |

(Continued)

FOREIGN PATENT DOCUMENTS

| | | | |
|---|---|---|---|
| EP | 3648903 | B1 | 4/2022 |
| WO | 2019007787 | A1 | 1/2019 |

OTHER PUBLICATIONS

Flores-Céspedes, et al., "Alginate-Bentonite-Based Hydrogels Designed to Obtain Controlled-Release Formulations of Dodecyl Acetate", Gels, vol. 9, Article 388, May 6, 2023, pp. 1-16.

(Continued)

*Primary Examiner* — Michael J Carey
*Assistant Examiner* — Maria Christina Talty
(74) *Attorney, Agent, or Firm* — Adler Pollock & Sheehan P.C.

(57) ABSTRACT

Disclosed are surgical apparatuses including a hydrogel-based ultrasonography probe stabilizer to enable ultrasound imaging of organs (e.g., the heart) during a surgery such as cardiac surgery. Procedures for ultrasonic imaging during surgery are also described such as contacting an organ with an ultrasonography probe stabilizer during a surgery such that the stabilizer is able to hold on to and dynamically conform to the organ (e.g., a rapidly beating heart) during surgery to provide clearer and wider view sonograms of dynamic, moving organs.

6 Claims, 3 Drawing Sheets

(56) References Cited

U.S. PATENT DOCUMENTS

2005/0240102 A1* 10/2005 Rachlin .................... A61B 8/10
600/459

OTHER PUBLICATIONS

Klucinec, Brian, "The Effectiveness of the Aquaflex Gel Pad in the Transmission of Acoustic Energy", Journal of Athletic Training, vol. 31, No. 4, 1996, pp. 313-317.

Yang, et al., "Strengthening Alginate/Polyacrylamide Hydrogels Using Various Multivalent Cations", ACS Applied Materials & Interfaces, vol. 5, No. 21, 2013, pp. 10418-10422.

Furnary AP, et al.; Initial clinical trial of substernal epicardial echocardiography: SEEing a new window to the postoperative heart. Ann Thorac Surg. Sep. 2001;72(3):S1077-82. doi: 10.1016/s0003-4975(01)02952-6. PMID: 11565730.

Reeves ST, et al.; American Society of Echocardiography; Society of Cardiovascular Anesthesiologists. Guidelines for performing a comprehensive epicardial echocardiography examination: recommendations of the American Society of Echocardiography and the Society of Cardiovascular Anesthesiologists. J Am Soc Echocardiogr. Apr. 2007;20(4):427-37. doi: 10.1016/j.echo.2007.01.011. PMID: 17400124.

* cited by examiner

HYDROGEL-BASED ULTRASONOGRAPHY PROBE STABILIZER

CROSS-REFERENCE TO RELATED APPLICATIONS

This application claims benefit from U.S. Provisional Patent Application Ser. No. 63/380,916, filed Oct. 25, 2022, which is incorporated by reference herein in its entirety.

FIELD OF THE INVENTION

The present invention relates to surgical methods and devices, and in one example, to a hydrogel-based ultrasonography probe stabilizer to enable epicardial ultrasound imaging during cardiac surgeries.

BACKGROUND OF THE INVENTION

In patients undergoing open heart surgery, intraoperative transesophageal echocardiography (TEE) is often utilized to assess heart function, valve function, and the aorta. Imaging findings can be essential to guide patient management to assess for technical success. TEE requires a probe to be inserted into the patient's esophagus to visualize the chambers of the heart posteriorly. However, approximately one out of two hundred patients may have a contraindication to TEE including but not limited to esophageal stricture, immunosuppression, steroid use, esophageal carcinoma, esophagitis, and bleeding disorders. In these patients, epicardial ultrasound may be used to visualize the structures of the heart. Unfortunately, the surface texture and anatomy of the heart makes stabilizing an ultrasound probe on its surface challenging, as the heart is in constant and varied motion. Thus, new methods and ultrasonic probe stabilization techniques are urgently needed for epicardial ultrasound and for critical visualizations during surgery.

SUMMARY OF THE INVENTION

The following presents a summary of the innovation to provide an introduction to some aspects of the invention. This summary is not an extensive overview of the invention. It is intended to neither identify key or critical elements of the invention nor delineate the scope of the invention. Its purpose is to present some concepts of the invention in as a prelude to the more detailed description that is presented later.

Disclosed is a surgical apparatus including a hydrogel-based ultrasonography probe stabilizer to enable epicardial ultrasound imaging during surgery. Cardiac surgery is exemplified herein, but the apparatuses and procedures could be applied to other surgeries. In one embodiment, an apparatus has been designed to overlay the heart, mold to its surface, and optimize the stability of an ultrasound probe thus improving the quality of acquired images. In another embodiment, a disclosed surgical apparatus includes a physical matrix interface to facilitate cardiac ultrasound probe image acquisition of patients during, for example, cardiac surgery, and particularly where TEE is contraindicated.

In an embodiment, the technology disclosed herein provides a method for acquiring an ultrasound image during a surgery, the method comprising the steps of: (1) providing a subject in an intraoperative surgery; (2) contacting an organ of the subject with a hydrogel-based ultrasonography probe stabilizer, whereby the hydrogel-based ultrasonography probe stabilizer adheres to the organ and forms a stable matrix interface between the organ and an acquisition probe; and (3) using the acquisition probe to acquire an image of the organ; wherein the stable matrix interface provides a stable and clear image while the organ moves in an unpredictable, rapid, erratic, and/or a beating movement.

The method described in the embodiment above can be wherein the hydrogel based ultrasonography probe stabilizer is operative to overlay a beating heart (e.g., or other moving organ), mold to its surface, and optimize the stability of an ultrasound probe, improving the quality, width of view, and/or clarity of acquired images during said movement compared to images acquired without the stabilizer. It is contemplated that such a method can be wherein TEE (intraoperative transesophageal echocardiography) is contraindicated for the subject.

The method can be, for example, wherein the organ includes a kinetic tissue, and the kinetic tissue is at the stable matrix interface between the organ and the acquisition probe.

In an embodiment, a surgical apparatus comprising a hydrogel-based ultrasonography probe stabilizer is disclosed (see Examples) to enable epicardial ultrasound during cardiac surgery; wherein the apparatus is operative to implement the methods described herein.

In an embodiment, the hydrogel-based ultrasonography probe stabilizer or matrix interface is flexible and moldable. In addition, the matrix interface is durable enough to support an ultrasound probe and biocompatible for placement on top of a beating heart during open heart surgery. In another embodiment, the matrix interface is created from materials optimized for transmitting ultrasound waves. In yet another embodiment, the matrix interface would solve the TEE contraindication problem that approximately 0.5 percent of patients face when undergoing open heart surgery.

During surgery, in order to evaluate surgical interventions, it is typically required to place ultrasound probes in multiple planes (e.g., seven) and unique positions which can be difficult and challenging especially on a beating heart. In some embodiments, because of the flexibility and moldability of the hydrogel-based ultrasonography probe stabilizer, the stabilizer provides a matrix interface that can be used in various planes and positions such that the ultrasound probes can be properly stabilized in order to facilitate accurate diagnosis and management of the patient acutely in surgery. In other embodiments, when resources are limited and surgery is performed without TEE, the presently disclosed hydrogel-based ultrasonography probe stabilizer can be used in conjunction with an ultrasound probe.

Presently disclosed embodiments may be used by cardiac surgeons performing open heart surgeries where the use of an ultrasound probe alone is more challenging than other surfaces. The risk of TEE use in patients would be reduced where TEE use is contraindicated (with risks ranging from esophageal tears to death) as well as reducing the difficulty associated with acquiring confirmatory ultrasound images on a beating heart with a slippery probe. It is contemplated that while a beating heart provides a readily discernable example of the concepts disclosed herein, the technology can be applied to fill other challenging visualization needs during surgeries.

In some embodiments, the disclosed apparatus would reduce the time needed to confirm surgical correction of the heart and expedite surgery closure. In other embodiments, the disclosed apparatus may be inserted into a plastic surgical sleeve for re-use or be disposable after a single use.

Disclosed embodiments are able to overcome any interaction shortfalls with surgical attempts to make contact with kinetic tissue (i.e., interface with moving tissue), especially while there are prior devices capable of handling incident tissue surfaces with the skin and other exterior surfaces, they are unable to address interfaces with internal organs such as the heart.

Disclosed embodiments can also be used without a need for a controller to aid in the confirmation of the matrix interface of the apparatus to the incident surface, and without the need to apply additional pressure to augment and avoid entrapment of air bubbles between the matrix interface and the apparatus. Specifically, the presently disclosed apparatus does not require the use of a controller and can be made of a homogenous layer consisting of or including the chemical composition described herein. In operation, a user need only apply pressure (via the user's hands) to conform the interface of the apparatus to the heart thus creating a process that intrinsically removes bubbles from the apparatus itself (not enhanced with a controller). In another example the matrix interface self-adheres to the organ to be visualized and remains in contact until removed by the surgeon or health care provider.

In one embodiment, the presently disclosed apparatus is not deformable to electromagnetic stimulus (e.g., via an ultrasound probe). While the presently disclosed apparatus is flexible and moldable, conduction of ultrasound waves through the apparatus does not deform the apparatus, e.g., change its density or thickness. While the presently disclosed apparatus does bend around convex or concave surfaces, it remains stable in its desired conductivity of visualizations/measurements throughout changing surfaces, and the stability in thickness allows for the user (e.g., the cardiac surgeon) to have standardized views of internal heart structures (e.g., heart valves) across a fixed thickness of the interface of the apparatus.

In one embodiment, a surgical apparatus includes a hydrogel-based ultrasonography probe stabilizer to enable epicardial ultrasound during cardiac surgery. In this embodiment, the probe stabilizer is a hydrogel-based matrix interface that is flexible and moldable and can exhibit the properties and characteristics as described herein.

These and other features and advantages will be apparent from a reading of the following detailed description and a review of the associated drawings. It is to be understood that both the foregoing general description and the following detailed description are explanatory only and are not restrictive of aspects as claimed.

BRIEF DESCRIPTION OF THE DRAWINGS

The invention will be more fully understood by reference to the detailed description, in conjunction with the following figures.

DETAILED DESCRIPTION OF THE INVENTION

Figure 1:
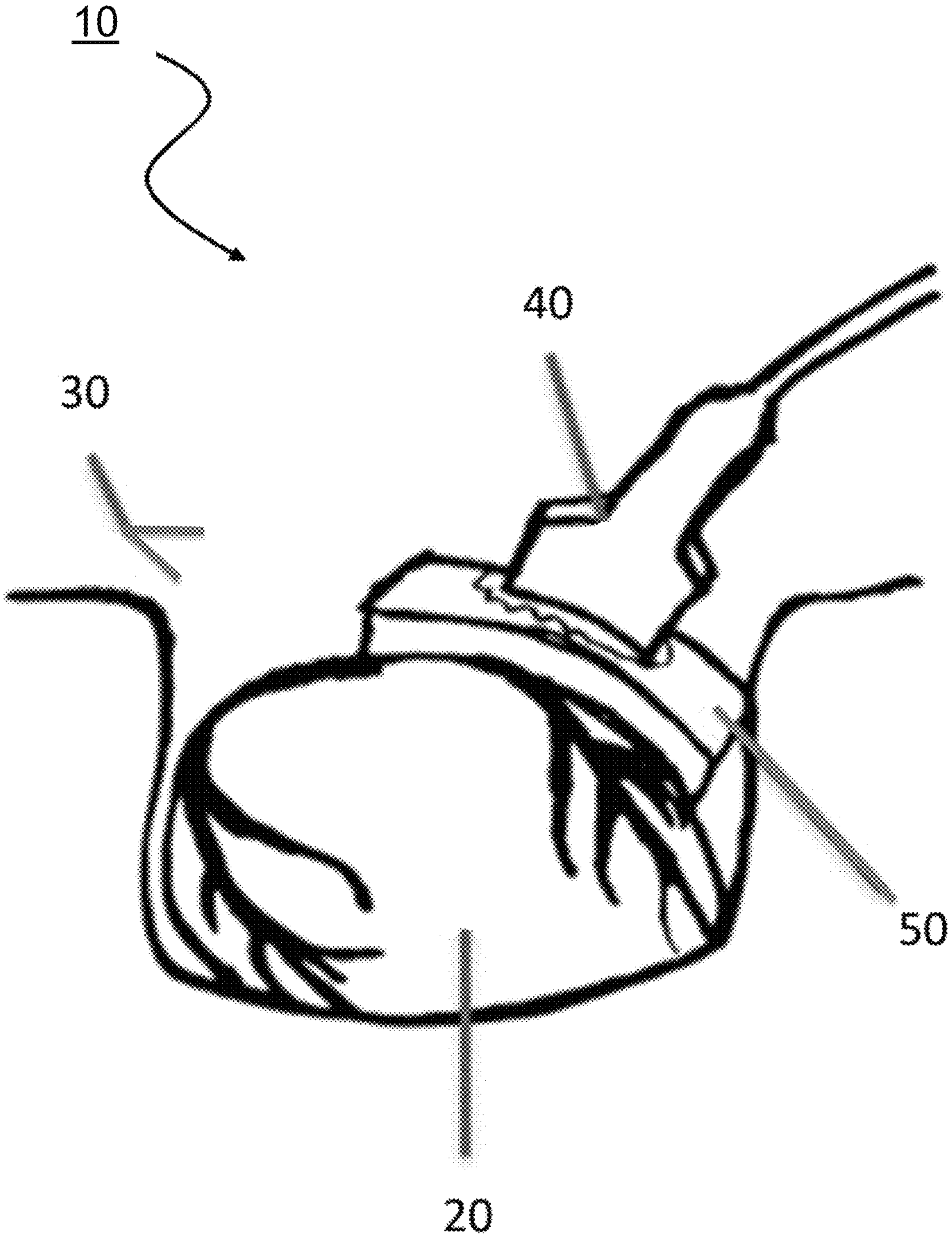
FIG. 1 is an in-situ example view of a surgical apparatus including a hydrogel-based ultrasonography probe stabilizer (matrix interface 50) in contact with a rapidly beating heart 20 to enable epicardial ultrasound imaging during cardiac surgery.

The subject innovation is now described with reference to the drawings, wherein like reference numerals are used to refer to like elements throughout. In the following description, for purposes of explanation, numerous specific details are set forth in order to provide a thorough understanding of the present invention. It may be evident, however, that the present invention may be practiced without these specific details. In other instances, the inventive concepts are described with Examples to provide insights into the hope inspiring and life-saving benefits of the invention.

FIG. 1 is an in-situ surgical view 10 of a surgical apparatus including a hydrogel-based ultrasonography probe stabilizer (matrix interface 50) to enable epicardial ultrasound imaging during cardiac surgery. The surgical view 10 illustrates a rapidly beating heart 20 accessed within an open mediastinum 30. An ultrasound probe 40 may be situated above the heart 20 being stabilized and held in an acquisition position by an epicardial matrix interface 50 according to an embodiment of the present disclosure.

In one embodiment, the epicardial matrix interface 50 can be hydrogel-based and function as an ultrasonography probe stabilizer to enable epicardial ultrasound imaging during cardiac surgery. In one embodiment, the hydrogel for forming the epicardial matrix interface 50 can include the following chemical composition (per 100 mL of water): about 1 g of sodium alginate, up to about 2 g of bentonite, about 6 g of acrylamide, about 0.25 to about 0.75 g of methylene bisacrylamide, and about 0.1 g of ammonium persulphate. In another example, per 100 mL of water can be added in the range from about 0.5 to about 2 g of sodium alginate, up to about 2 or 3 g of bentonite, a range from about 3 g to about 9 g of acrylamide, about 0.1 to about 1 g of methylene bisacrylamide, and about 0.05 to about 0.5 g of ammonium persulphate.

In some embodiments, the chemical compositions (per 100 mL of water) can include: from about 0.1 g to about 4 g of sodium alginate, from about 0.1 g to about 4 g of bentonite, from about 1 g to about 10 g of acrylamide, from about 0.1 to about 2.0 g of methylene bisacrylamide, and up to about 1 g of ammonium persulphate.

In one embodiment, the chemical composition of the epicardial matrix interface hydrogel 50 optimizes the opposing properties of adhesiveness and shear-ability required to stabilize an ultrasound probe 40 while accommodating for the motion of a beating heart 20 (e.g., a non-static matrix interface). In some embodiments, the shape, size, and weight of the epicardial matrix interface hydrogel 50 can be designed to accommodate the size constraints of the chest cavity during open heart surgery in order to avoid compressing the open heart 20.

In one embodiment, the moldability of the epicardial matrix interface hydrogel 50 has been designed to allow flexible approximation of the contours of the surface of the heart 20 and thereby vessels thereof (e.g., aorta and pulmonary artery). And because the epicardial matrix interface hydrogel 50 is biocompatible, it can be used in direct contact with exposed cardiac tissues. In addition, because the hydrogel is sterilizable, it can be used in an open body cavity within a sterile surgical environment.

Figure 2:
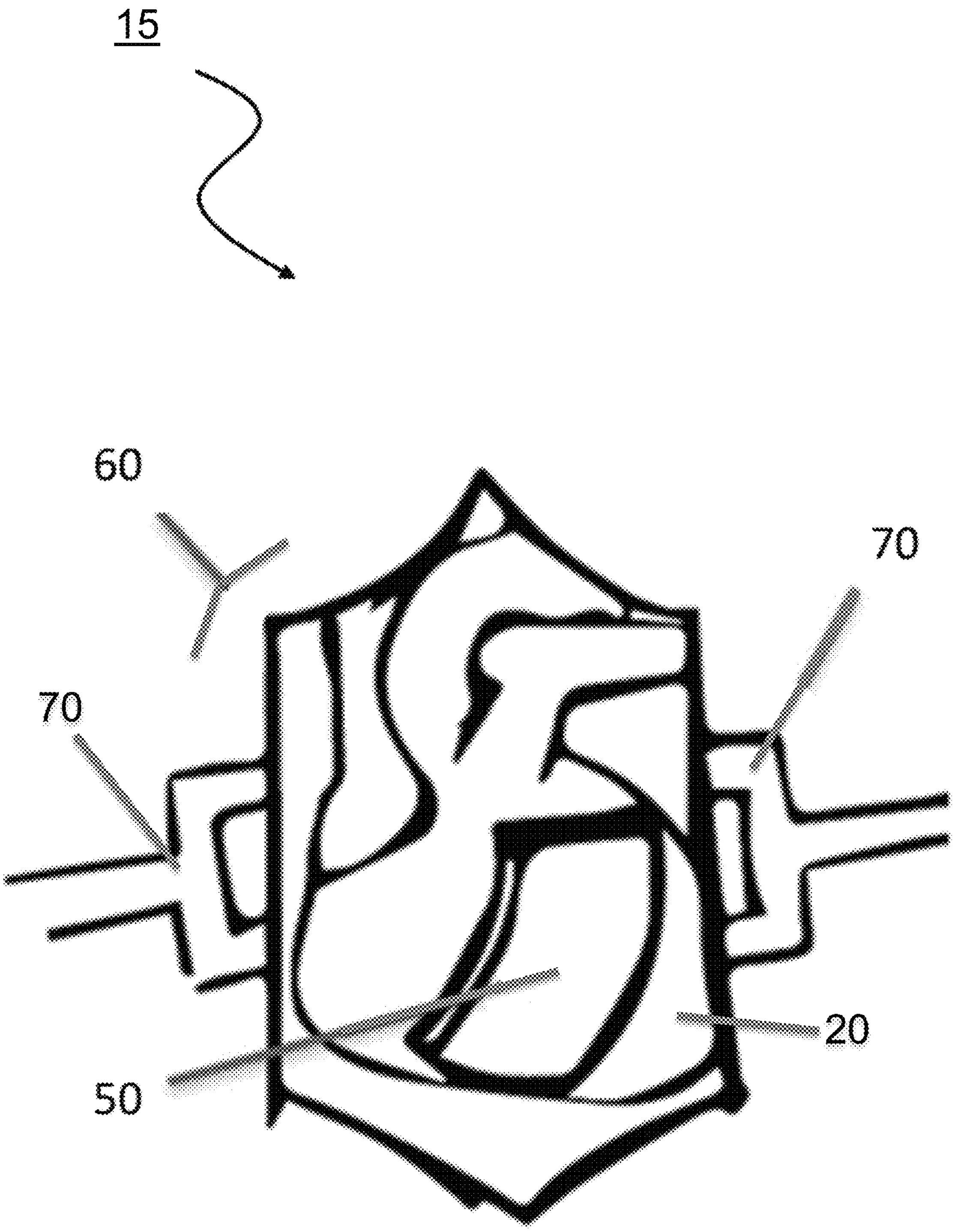
FIG. 2 is a top-down surgical view of a hydrogel-based ultrasonography probe stabilizer (matrix interface 50) in contact with a rapidly beating heart 20 during a surgical procedure with retractors 70 in surgical positions.

FIG. 2 is a top-down surgical view 15 of the example view of FIG. 1. In this instance, the top-down view 15 shows the epicardial matrix interface 50 in action through a surgical window 60 including the retractors 70 such as those used for grasping, retaining or holding back tissues during surgical procedures. The ultrasound probe 40 (FIG. 1) is not shown in this view so that the epicardial matrix interface 50 can be seen on the rapidly beating heart 20. The surgical window 60 is provided by the hold of the retractors 70. Because of the moldability and the flexibility of the epicardial matrix interface 50, the surgical apparatus can be used in various planes and positions. For example, in vertical or horizontal planes, or other planes in between. And because of the flexibility of the epicardial matrix interface 50, the surgical apparatus is able to conform to the shape of the heart or any other internal organs where the ultrasound probe or other apparatuses (e.g., retractors 70) may need to be positioned for imaging or other purposes.

While FIG. 2 provides a surgeon's view 15 of the rapidly beating heart 20, as such, a method for acquiring an ultrasound image of a moving organ can be described as: providing a subject; accessing a moving organ in the subject; contacting the organ with a hydrogel-based ultrasonography stabilizer (matrix interface 50), whereby the matrix interface 50 is operative to adhere to the organ during rapid movements or pauses (e.g., stationary rests) of the organ; contacting the matrix interface with a probe (e.g., ultrasound probe 40 in FIG. 1); and acquiring an image through the matrix interface 50. Surprisingly, the image is vastly improved when compared to past technologies. The technology disclosed herein contemplates, on one end of an example, the matrix interface 50 can be used during a life-saving intervention by a healthcare professional and then discarded. On another end of an example, the technology disclosed herein contemplates the matrix interface 50 could be implantable in a subject for treatment, diagnosis or monitoring. In some examples, the matrix interface 50 can be penetrated (e.g., by a needle) and is "self-healing" so as describe in that whereby the matrix interface continues to adhere and operate as a clear transducer, providing improved imaging, after the penetration.

Figure 3:
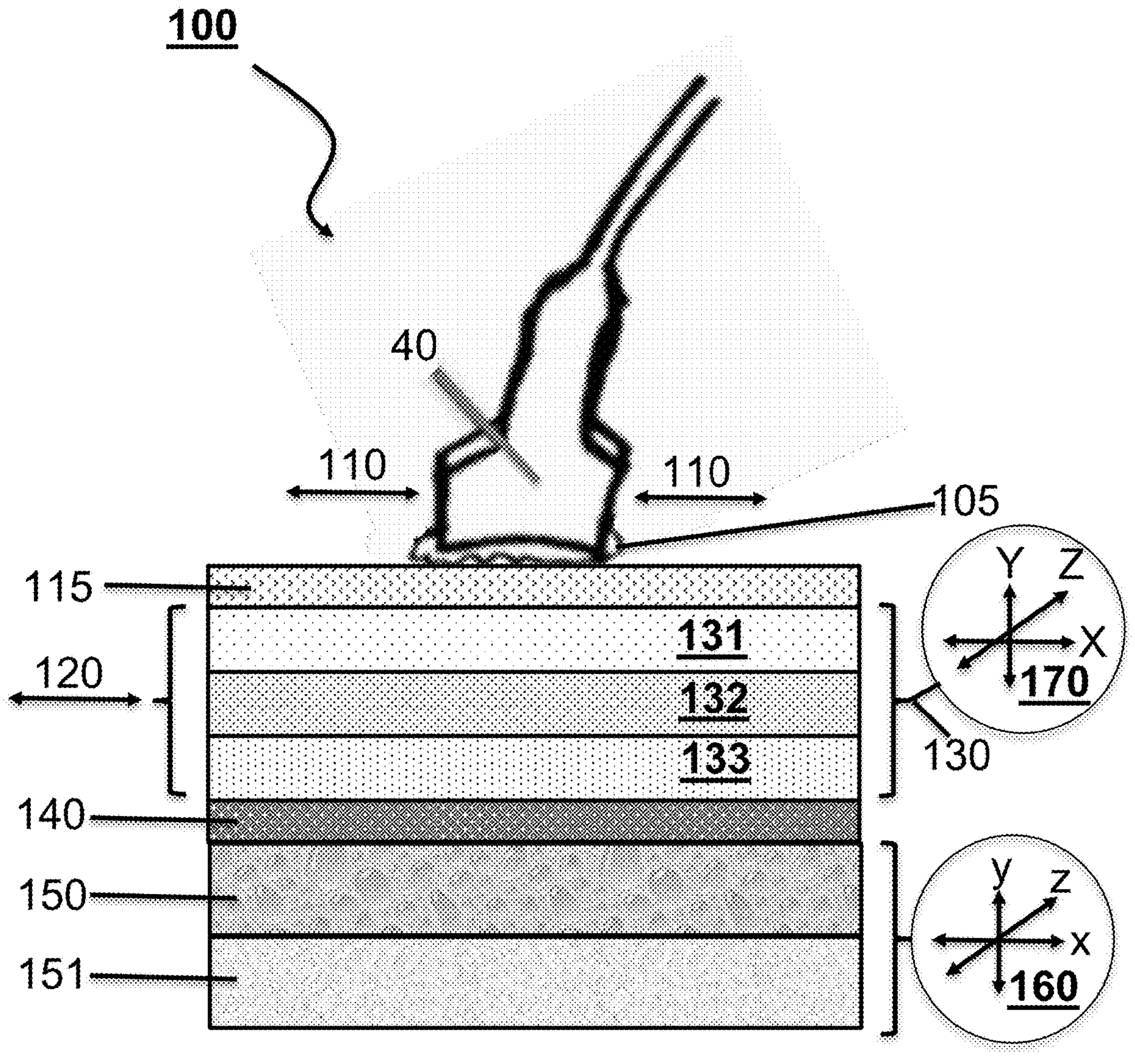
FIG. 3 shows dynamic variable action 100 during data acquisition by a cross-sectional view of a matrix interface 130 in contact with a dynamically moving organ 150 (e.g., a heart) and/or an optional kinetic outer tissue 151 as the organ 150 moves in an unpredictable, rapid, erratic, and/or a beating movement 160 and the matrix interface adheres, follows, stabilizes, and/or dampens such movement at 170 to provide a stable and clear ultrasound image and a stable matrix interface at probe 40.

FIG. 3 depicts action and movement during an acquisition of an ultrasound image 100, FIG. 3 shows a cross-sectional view of a matrix interface 130 in contact with a dynamically moving organ 150 (e.g., a heart) and/or an optional kinetic outer tissue 151. It should be understood that organ 150 depicted in FIG. 3 can represent the rapidly beating heart 20 depicted in FIG. 1 and FIG. 2. It is contemplated that organ 150 can represent a moving organ such as (the non-limiting examples of) an eye, a stomach/intestine, a muscle, a lung, or a heart. In another example, the organ 150 can be representative of a subject, such as a rapidly moving newborn, who is in need of imaging but who moves constantly without stopping. The kinetic outer tissue 151 can be representative of a muscular outer tissue, an outer skin, or an epicardium.

Referring to FIG. 3, as the organ 150 and the (optional) kinetic tissue 151 moves in an unpredictable, rapid, erratic, and/or a beating movement at 160, the matrix interface adheres, follows, stabilizes, and/or dampens such movement at 170 (i.e., stabilization). The movements (x,y,z) at 160 can be followed (X,Y,Z) at 170 with adherence to the organ 150 by the matrix interface 130 and a complete stabilization is provided for the probe 40 to be smoothly moved 110 during the dynamic acquisition 100. The various movements of the ultrasound probe can be referred to as rocking, fanning/tilting, sliding, and/or rotating, all of which are enabled/possible with our device 50 and stabilization 170 in place. Surprisingly, the matrix interface 130 (or hydrogel-based ultrasonography probe stabilizer) is operating to provide a stable and clear ultrasound image and a stable matrix interface to the probe 40, even when tested on a rapidly moving hand. It is suspected that such convenience will save lives in providing much needed imaging of dynamic organs. During the stabilization 170, the probe 40 can be moved 110 over and about the hydrogel-based ultrasonography probe stabilizer 130 (with one or more layers represented by 131, 132, 133). While the movement of the probe 40 at arrows 110 indicates left/right movement, it should be understood that the probe 40 can be moved in the x, y, and z axes while acquisition is done.

An ultrasound probe gel (optional) 105 can be disposed immediately underneath the probe 40. Another ultrasound gel 115 (optional) can be disposed at an outer layer of the hydrogel-based ultrasonography probe stabilizer. Similarly, an optional organ interface layer of hydrogel-based ultrasonography probe stabilizer 140 can be applied between the hydrogel-based ultrasonography probe stabilizer 130 and organ 150. The optional organ interface layer 140 can include, for example, buffers, adhesive, and/or moisture from the actual organ 150 and can allow a movement 120 of the entire hydrogel-based ultrasonography probe stabilizer 130 along/across the organ 150 as the data acquisition takes place. While the movement 120 of the stabilizer 130 indicates left/right movement, it should be understood that the stabilizer 130 can be moved in the x, y, and z axes while acquisition is done and as the stabilization 170 takes place.

While example embodiments have been particularly shown and described, it will be understood by those skilled in the art that various changes in form and details may be made therein without departing from the scope of the embodiments encompassed by the appended claims. For example, other useful implementations could be achieved if steps of the disclosed techniques were performed in a different order and/or if components in the disclosed systems were combined in a different manner and/or replaced or supplemented by other components. Accordingly, other implementations are within the scope of the disclosure.

EXAMPLES

Example 1. Investigating Potential-Commercialization Prototypes of Hydrogel-Based Ultrasonography Probe Stabilizer The hydrogel-based ultrasonography probe stabilizer is a much needed, groundbreaking medical innovation designed to, for example, enable intraoperative epicardiac ultrasound for cardiac surgery patients for whom intraoperative transesophageal echocardiography (TEE) is contraindicated or cannot be performed for technical reasons. By enabling high-quality intraoperative ultrasonographic visualization of cardiac function for all patients, this device ultimately improves patient cardiac surgical care and patient outcomes (i.e., saves lives). It is discerned that by enabling high-quality intraoperative ultrasonic visualization during many other surgeries, the technology disclosed herein rapidly becomes more widespread in use because surgeons find it adaptable and easy to use.

Experimental models have been made. Materials are ordered and more functional prototypes of the matrix interface 50 (FIG. 2) are made, along with an entire device. We have made a functioning model. Work is done to create more models to vary different parameters (e.g., texture, shear-ability, thickness and shape).

Demonstrations of the technology are provided to show how the methods described herein are intuitively learned and rapidly implemented to save lives. A demonstration video is produced for educational, remote, and emergency use purposes.

Example 2. Production of Sample Ultrasonography Probe Stabilizer

A hydrogel for forming the epicardial matrix interface 50 (FIG. 2) is made including the following chemical composition (per 100 mL of water): about 1 g of sodium alginate, up to about 2 g of bentonite, about 6 g of acrylamide, about 0.25 to about 0.75 g of methylene bisacrylamide, and about 0.1 g of ammonium persulphate. Gels formed from carbomer, (mono)propylene glycol, and triethanolamine are applied to the stabilizer, and the organ to be tested. A probe is slid over the stabilizer with and without a gel. Referring to FIG. 3, various thicknesses of the hydrogel-based ultrasonography probe stabilizer with one or more layers 130 are tried. The thickness of each optional layer 131, 132, and 133 can be in a range from about 0.5 mm to about 2 cm, about 1 mm to about 0.5 cm, or about 2 mm to about 0.4 cm. The thickness of the hydrogel-based ultrasonography probe stabilizer with one or more layers 130 can be optionally in a range from about 0.5 mm to about 20 cm, in the range from about 0.5 mm to about 10 cm, or in the range from about 0.5 mm to about 5 cm. Various shapes and sizes are fabricated.

Example 3. Testing of Ultrasonography Probe Stabilizer

At least two other prototypes are made (Example 1). The various devices and matrix interfaces 50 (FIG. 2) are tested on a pig model (i.e., fresh pig hearts attached to mechanical pumps or stimulating electrodes to cause it to beat) that we hope to complete within the next few months. We are also working on finding an adequate sterilization method, but this is still under development.

Example 4. Testing of Layers with Ultrasonography Probe Stabilizer

An experimental model from Example 1 is applied to an organ 150 as depicted in FIG. 3. Another layer from another model is pressed with the first experimental model to form a hydrogel-based ultrasonography probe stabilizer with one or more layers 130 depicted in FIG. 3 (optional layers 131, 132, 133). In another experiment, different mixtures of hydrogel are sequentially dispensed into a mold shape to form a layered stabilizer 130, to provide optional layers 131, 132, 133. An entirely monolithic stabilizer 130 is also produced and tested. A sterilizing layer 140 (FIG. 3) is fabricated. During these experiments, the capability of the hydrogel-based ultrasonography probe stabilizer with one or more layers 130 to follow an unpredictable rapid, erratic, and/or beating movement of the organ 160 is found to stabilize 170 and provide a life-saving acquisition for the probe 40 with ease of movement 110 of the probe.

REFERENCES

Hilberath, J, Oakes, D, Shernan, S, Bulwer, B, D'Ambra, M, and Eltzschig, H. Safety of Transesophageal Echocardiography. *Journal of the American Society of Echocardiography.* 2010 Nov. 1, 23(11):1115-1127.

Miller-Hance, W, Puchalski, M, and Ayers, N. Indications and Guidelines in Pediatric and Congenital Heart Disease, in *Transesophageal Echocardiography for Pediatric and Congenital Heart Disease.* 2021. ISBN: 978-3-030-57192-4

Khandheria B K, Seward J B, Bailey K R. Safety of transesophageal echocardiography: experience with 2070 consecutive procedures. *J Am Coll Cardiol* 1991; 17: 20A.

The invention claimed is:

1. A method for acquiring an ultrasound image during an intraoperative surgery, the method comprising the steps of:

(a) providing a subject undergoing the intraoperative surgery;

(b) during the intraoperative surgery, exposing an organ of the subject, wherein the organ is a beating heart that is exposed during the intraoperative surgery;

(c) providing a physical matrix interface comprising a hydrogel-based ultrasonography probe stabilizer that is flexible, moldable, and is durable enough to support an ultrasound probe, and is biocompatible for placement on top of the beating heart during the intraoperative surgery;

(d) disposing an organ interface layer on an outer surface of the beating heart, wherein the organ interface layer comprises at least one of a buffer, an adhesive, or moisture from the beating heart, and contacting the organ interface layer with the hydrogel-based ultrasonography probe stabilizer on the outer surface of the beating heart such that the stabilizer adheres to the beating heart and forms a stable matrix interface between the beating heart and the ultrasound probe, wherein the stabilizer comprises a homogenous hydrogel layer that includes, per 100 ml of water, 0.1 g to 4 g of sodium alginate, up to 3 g of bentonite, 3 g to 9 g of acrylamide, 0.1 g to 1 g of methylene bisacrylamide, and 0.05 g to 0.5 g of ammonium persulphate; whereby the organ interface layer is configured to allow a movement of the entire hydrogel-based ultrasonography probe stabilizer along and/or across the beating heart;

(e) applying pressure to the stabilizer to conform the stabilizer to the beating heart and remove entrapped air bubbles from the stable matrix interface without use of a controller;

(f) disposing (i) an ultrasound gel on a probe-facing outer surface of the stabilizer which contacts the organ interface layer from step (d) on a probe-facing outer surface of the stabilizer, and disposing (ii) an ultrasound probe gel between the ultrasound probe and the probe-facing outer surface of the stabilizer;

(g) placing the ultrasound probe on the stabilizer and using the ultrasound probe to acquire an ultrasound image of the beating heart through the stabilizer;

(h) while acquiring the ultrasound image, while the beating heart moves in an unpredictable, rapid, or erratic movement of the beating heart, moving the ultrasound probe relative to the stabilizer by at least one of rocking, fanning/tilting, sliding, or rotating, while the stabilizer follows movement of the beating heart and provides stabilization at the stable matrix interface; and (i) wherein conduction of ultrasound waves through the stabilizer and the stable matrix interface does not deform the interface, does not require an additional pressure to avoid an entrapment of air bubbles between the matrix interface and the probe, and does not change a density or thickness of the stabilizer.

2. The method of claim 1, wherein contacting the outer surface of the beating heart with the hydrogel-based ultrasonography probe stabilizer comprises overlaying the hydrogel-based ultrasonography probe stabilizer on the beating heart such that, because the stabilizer is flexible and moldable, the stabilizer conforms to the surface of the beating heart and remains adhered thereto during the unpredictable, rapid, erratic, or beating movement, and wherein the organ interface layer permits translation of the stabilizer along and across the beating heart during data acquisition such that the ultrasound probe is positionable in a plurality of planes and positions while maintaining the stable matrix interface, and wherein the stabilizer maintains a fixed thickness during conduction of ultrasound waves such that standardized views of internal heart structures are obtainable across the fixed thickness of the stable matrix interface, thereby improving the quality, width of view, and/or clarity of acquired images during said movement compared to images acquired without the stabilizer.

3. The method of claim 2, wherein (intraoperative transesophageal echocardiography (TEE) is contraindicated for the subject.

4. The method of claim 2, wherein the stabilizer has a thickness in a range from 0.5 mm to 5 cm and comprises one or more layers each having a thickness in a range from 0.5 mm to 2 cm.

5. The method of claim 1, wherein the beating heart includes a kinetic tissue, and the kinetic tissue of the beating heart is at the stable matrix interface between the beating heart and the ultrasound probe.

6. A surgical apparatus for epicardial ultrasonography during an intraoperative surgery of a subject, comprising:

(a) a hydrogel-based ultrasonography probe stabilizer defining a physical matrix interface and having a probe-facing outer surface and a heart-facing inner surface, the stabilizer being flexible, moldable, and configured to be durable to support an ultrasound probe, and biocompatible for placement on top of a beating heart during the intraoperative surgery;

(b) an organ interface layer configured to be disposed on an outer surface of the beating heart, wherein the organ interface layer comprises at least one of a buffer, an adhesive, or moisture from the beating heart;

(c) wherein the stabilizer comprises a homogenous hydrogel layer that includes, per 100 ml of water, 0.1 g to 4 g of sodium alginate, up to 3 g of bentonite, 3 g to 9 g of acrylamide, 0.1 g to 1 g of methylene bisacrylamide, and 0.05 g to 0.5 g of ammonium persulphate;

(d) an ultrasound gel disposed on the probe-facing outer surface of the stabilizer;

(e) an ultrasound probe gel configured to be disposed between the ultrasound probe and the probe-facing outer surface of the stabilizer;

(f) the ultrasound probe;

wherein, during use in the intraoperative surgery with the beating heart of the subject exposed: the stabilizer is configured to contact the organ interface layer on the outer surface of the beating heart such that the stabilizer adheres to the beating heart and forms a stable matrix interface between the beating heart and the ultrasound probe; the organ interface layer is configured to allow a movement of the stabilizer along and/or across the beating heart;

wherein the apparatus is configured such that a user applies pressure to the stabilizer to conform the stabilizer to the beating heart and remove entrapped air bubbles from the stable matrix interface without use of a controller wherein the ultrasound probe is configured to be placed on the stabilizer and to acquire an ultrasound image of the beating heart through the stabilizer;

wherein, while acquiring the ultrasound image, while the beating heart moves in an unpredictable, rapid, or erratic movement of the beating heart, the ultrasound probe is movable relative to the stabilizer by at least one of rocking, fanning/tilting, sliding, or rotating, while the stabilizer is configured to follow movement of the beating heart and provide stabilization at the stable matrix interface; and wherein conduction of ultrasound waves through the stable matrix interface does not deform the interface, does not require an additional pressure to avoid an entrapment of air bubbles between the matrix interface and the probe, and does not change a density or thickness of the stabilizer.

* * * * *